US00PP29953P2

(12) United States Plant Patent
Pierce

(10) Patent No.: US PP29,953 P2
(45) Date of Patent: Dec. 4, 2018

(54) ***CALIBRACHOA* PLANT NAMED 'CBRZ0011'**

(50) Latin Name: *Calibrachoa hybrida*
Varietal Denomination: CBRZ0011

(71) Applicant: SYNGENTA PARTICIPATIONS AG, Basel (CH)

(72) Inventor: Robert O. Pierce, Watsonville, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,923

(22) Filed: Aug. 23, 2017

(51) Int. Cl.
*A01H 5/02* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — Dale Skalla

(57) ABSTRACT

A new *Calibrachoa* plant named 'CBRZ0011' particularly distinguished by the mid-sized purple flowers with a darker "eye" and yellow inside the flower at the base of the petals, green foliage, good branching, late flowering, and a moderately compact, semi-trailing plant habit, and has little sensitivity to soil pH.

1 Drawing Sheet

Latin name of the genus and species of the plant claimed: *Calibrachoa hybrida.*

Varietal denomination: 'CBRZ0011'.

BACKGROUND OF THE NEW PLANT

The present invention comprises a new *Calibrachoa*, botanically known as *Calibrachoa hybrida*, and hereinafter referred to by the variety name 'CBRZ0011'.

'CBRZ0011' is a product of a planned breeding program. The new cultivar has mid-sized purple flowers with a darker "eye" and yellow inside the flower at the base of the petals, green foliage, good branching, late flowering, and a moderately compact, semi-trailing plant habit, and has little sensitivity to soil pH.

'CBRZ0011' originated from a hybridization made in December 2010 in a greenhouse in Gilroy, Calif., USA. The female parent was a clone identified as 'CAL2568-2' with a deep blue flower. The male parent of 'CBRZ0011' was proprietary plant characterized as a mid-blue flowered plant, known as '2529-4'. 'CBRZ0011' originated from a seedling selected in Gilroy, Calif.

The resulting seeds were sown in March 2011 and 'CBRZ0011' was selected as one flowering plant within the progeny of the stated cross in June 2011 in a controlled environment in Gilroy, Calif.

The first act of asexual reproduction of 'CBRZ0011' was accomplished when vegetative cuttings were propagated from the initial selection in the fall of 2011 in a controlled environment in Gilroy, Calif.

BRIEF SUMMARY OF INVENTION

Horticultural examination of plants grown from cuttings of the plant initiated in the spring of 2012, and continuing thereafter, has demonstrated that the combination of characteristics as herein disclosed for 'CBRZ0011' are firmly fixed and are retained through successive generations of asexual reproduction.

'CBRZ0011' has not been observed under all possible environmental conditions. The phenotype may vary significantly with variations in environment such as temperature, light intensity, and day length.

A Plant Breeder's Right for this cultivar was applied for in the European Union on Aug. 10, 2017, No. 2017/1998. 'CBRZ0011' has not been made publicly available prior to the effective filing date of this application, notwithstanding any disclosure that may have been made less than one year prior to the effective filing date of this application by the inventor or another who obtained 'CBRZ0011' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

Figure 1:
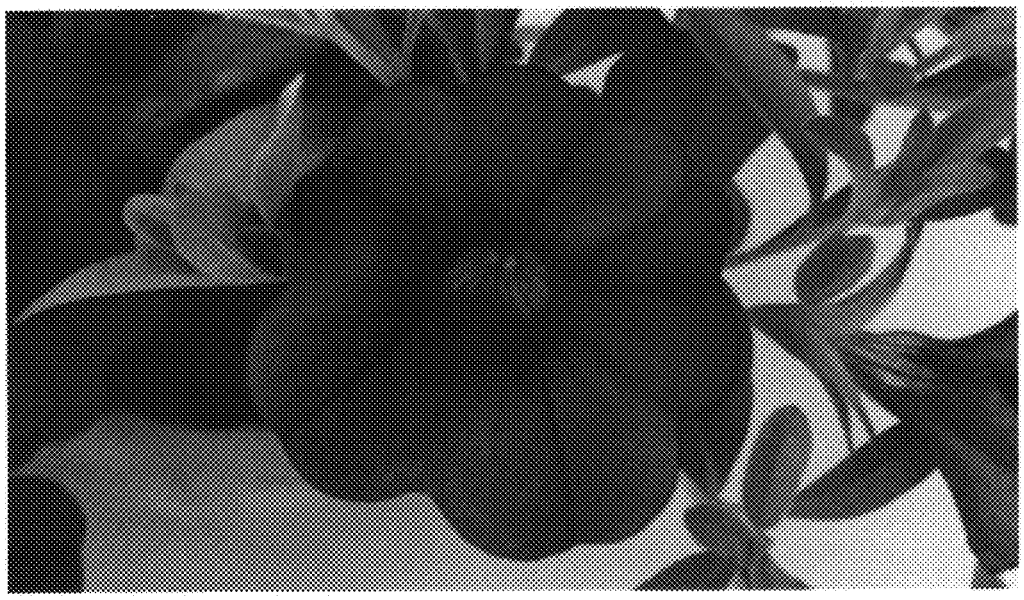
Figure 2:
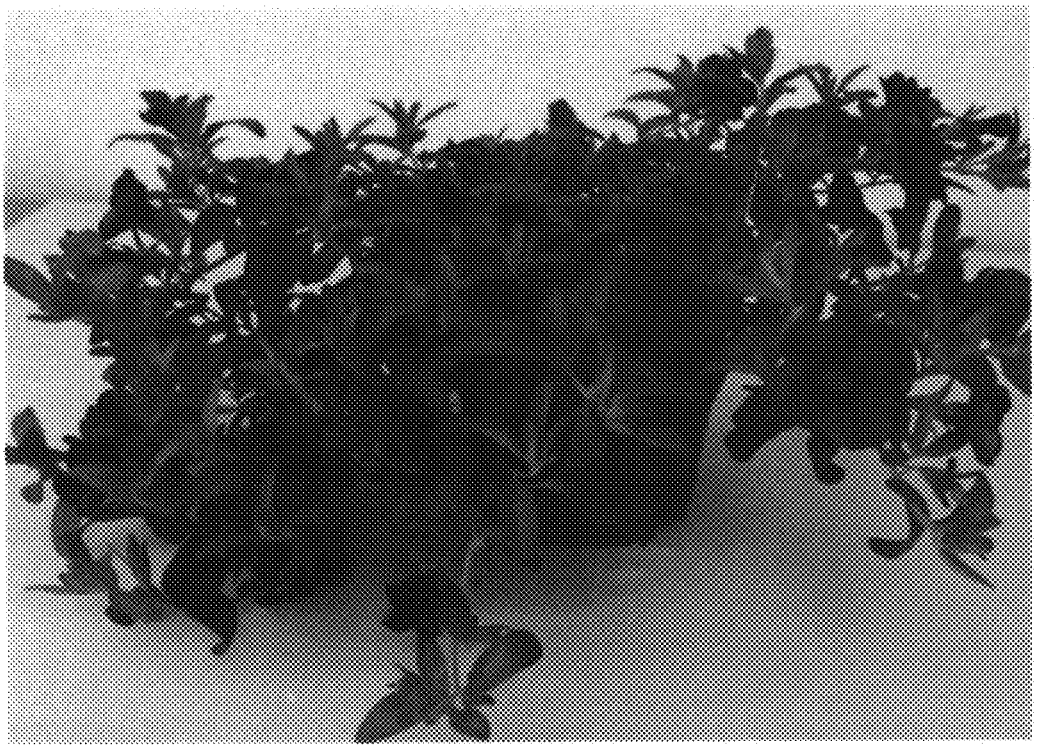

The accompanying photographic drawing shows typical flower and foliage characteristics of 'CBRZ0011' with colors being as true as possible with an illustration of this type. The photographic drawing shows in FIG. 1 shows a close-up of the flowers and in FIG. 2 is of a flowering plant of the new variety.

DETAILED BOTANICAL DESCRIPTION

The aforementioned photographs were taken in April 2017 in Gilroy, Calif.

The measurements and observations were made in Gilroy, Calif. on plants grown in an indoor trial.

Color references are made to The Royal Horticultural Society Colour Chart (R.H.S.) 2001.

TABLE 1

DIFFERENCES BETWEEN THE NEW VARIETY 'CBRZ0011' AND A SIMILAR VARIETY

| | 'CBRZ0011' | 'Callie Dark Blue' |
|---|---|---|
| Main flower color: | Purple | Blue |
| Color of throat: | Yellow | Dark blue |
| Plant habit as a young plant: | Semi upright then trailing | Trailing |

Plant:

*Form, growth and habit*.—Semi-upright stems, compact and mounding, very well branched.

*Plant height*.—7-9 cm.

*Plant height* (*inflorescence included*).—7-9 cm.

*Plant width*.—35-40 cm.

*Quantity of main branches*.—16-20.

*Quantity of secondary branches*.—4-6 per basal branch.

*Time to produce a flowering plant*.—7-8 weeks for a 12 cm pot (from planting of rooted cuttings).

Roots:

*Number of days to initiate*.—18-21 days at about 22° C.

*Number of days to produce a rooted cutting*.—21-24 days at 22° C.

*Type*.—Fibrous.

*Color*.—RHS 158D.

Stem:

*Color of stem*.—Mainly RHS 144A.

*Length of stem*.—Approximately 10-15 cm.

*Diameter*.—0.15-0.2 cm.

*Length of internodes*.—0.5-1.7 cm.

*Texture*.—Smooth, with hairs.

Foliage:

*Immature leaf, color of upper surface*.—RHS 144A.

*Immature leaf, color of lower surface*.—RHS 144A.

*Mature leaf, color of upper surface*.—RHS 137A.

*Mature leaf, color of lower surface*.—RHS 138A.

*Leaf blade, length*.—3.2-4.5 cm.

*Leaf, width*.—0.8-2.0 cm.

*Shape*.—Elliptical, narrow.

*Base shape*.—Attenuate.

*Apex shape*.—Obtuse.

*Margin*.—Entire.

*Texture*.—Hairs.

*Color of veins, upper surface*.—RHS 138B.

*Color of veins lower surface*.—RHS 138B.

*Petiole color*.—RHS 144B.

*Petiole length*.—0.1-0.3 cm.

*Diameter of petiole*.—0.1 cm.

*Texture*.—Smooth with hairs.

Inflorescence:

*Type*.—Flowers solitary in upper leaf axis and slanting upright or outwards.

*Quantity of inflorescences per plant*.—Approximately 30-40.

*Lastingness of individual flowers*.—About 7-9 days.

*Fragrance*.—None.

*Duration of flowering*.—Continuous flowering throughout the summer.

Pedicel:

*Color of pedicel*.—RHS 144A.

*Length of pedicel*.—1.-1.9 cm.

*Diameter of pedicel*.—1.0 mm.

*Texture of pedicel*.—With hair.

Flower:

*Immature flowers, corolla upper surface*.—RHS 83B.

*Immature flowers, corolla lower surface*.—RHS 83B overlain with RHS 155D.

*Mature flowers, color upper surface*.—RHS 81A with a somewhat deeper, purple ring, RHS 83A in the center around the throat opening. Deep in throat is a yellow color RHS 154B.

*Mature flowers, color lower surface*.—RHS 83B overlain with RHS 155D.

*Flower horizontal diameter*.—3.3-3.6 cm.

*Flower height* (*vertical*).—2.5-3.0 cm.

*Corolla tube length*.—About 1.1 cm.

*Petal apex shape*.—Retuse.

*Margin*.—Entire.

*Waviness of petals*.—Weak to medium.

*Petal lobation*.—Moderate.

*Corolla texture*.—'Face' papillose and glabrous; rear side with short hair.

*Corolla tube color inside*.—RHS 2B with RHS 83B veins.

*Corolla tube color outside*.—RHS 1C with RHS 83B veins.

Bud (just before opening):

*Color at apex*.—RHS 83A.

*Length*.—2.0-2.5 cm.

*Width* (*upper end*).—0.6-0.9 cm.

*Shape*.—Oblong.

Calyx:

*Number of sepals*.—5.

*Color of sepals, adaxial or upper surface*.—Closest to RHS 143A.

*Color of sepals, abaxial or lower surface*.—Closest to RHS 143AC.

*Length of sepals*.—1.2-1.7 cm.

*Width of sepals*.—0.2-0.4 cm.

*Sepal shape*.—Lanceolate.

*Apex shape*.—Obtuse to acute.

*Margins*.—Entire.

*Texture*.—Hairs.

Reproductive organs:

*Pistil*.—1.

*Length*.—1.3 cm.

*Style color*.—RHS 145B.

*Style length*.—0.8-0.9 cm.

*Stigma color*.—RHS 144B.

*Number of stamens*.—5.

*Color of filaments*.—RHS 4D.

*Length filaments*.—0.7-1.1 cm.

*Color of pollen*.—RHS 13B.

*Pollen amount*.—Moderate.

*Fertility/seed set*.—Not observed on this hybrid.

*Disease/pest resistance*.—Not observed on this hybrid.

What is claimed is:

1. A new and distinct variety of *Calibrachoa* plant named 'CBRZ0011', substantially as illustrated and described herein.

* * * * *